United States Patent [19]

Story

[11] 4,058,911

[45] Nov. 22, 1977

[54] ROAD-RUNNER ALCOHOL SAFETY INTERLOCK SYSTEM

[75] Inventor: Anne W. Story, Cambridge, Mass.

[73] Assignee: The United States of America as represented by the Secretary of the Department of Transportation, Washington, D.C.

[21] Appl. No.: 715,424

[22] Filed: Aug. 18, 1976

[51] Int. Cl.² .............................................. G09B 19/00
[52] U.S. Cl. ..................................... 35/22 R; 180/99
[58] Field of Search ................. 35/11 R, 11 A, 12 D, 35/12 W, 22 R; 128/2 N; 180/99; 235/184, 193; 273/1 E; 340/52, 53, 279; 351/17, 30, 36, 39

[56] References Cited

U.S. PATENT DOCUMENTS

| 3,311,995 | 4/1967 | Hudson ............................ 35/12 K |
| 3,358,130 | 12/1967 | Miura et al. ..................... 235/193 X |
| 3,483,302 | 12/1969 | Ashkenas et al. ............... 35/22 R X |
| 3,594,921 | 7/1971 | Quicker ............................ 35/11 R |
| 3,833,759 | 9/1974 | Yatabe ............................. 35/12 N X |
| 3,861,790 | 1/1975 | Tamura ............................ 35/22 R X |
| 3,883,962 | 5/1975 | Kunig ............................... 180/99 X |
| 3,918,176 | 11/1975 | Abernethy et al. .............. 35/22 R |

Primary Examiner—William H. Grieb
Assistant Examiner—Vance Y. Hum
Attorney, Agent, or Firm—Herbert E. Farmer; Harold P. Deeley, Jr.; Otto M. Wildensteiner

[57] ABSTRACT

An apparatus for determining a test subject's level of intoxication. Included is a display visible to the test subject and in which is produced by test equipment a pair of randomly moving, spaced apart objects. The test subject operates an actuator to indicate his selections of changing imaginary positions in the display having a predetermined constant spatial relationship to the moving objects. Dynamically determined by a computer system are the actual locations of those positions which are compared with the test subject's selections. Because of the requirement for determining imaginary positions by mental extrapolation, a very rigorous test of the subject's psychomotor capability is obtained.

7 Claims, 4 Drawing Figures

ROAD-RUNNER ALCOHOL SAFETY INTERLOCK SYSTEM

ORIGIN OF THE INVENTION

The invention described herein was made by an employee of the United States Government and may be manufactured and used by or for the Government for Governmental purposes without the payment of any royalties thereon or therefor.

BACKGROUND OF THE INVENTION

This invention relates generally to an apparatus for testing psychomotor capability and, more specifically, to an apparatus for testing intoxication levels.

Devices interconnected with the ignition systems of motor vehicles to test for sobriety prior to vehicle operation are known. However, the prior art devices measured sobriety by performance of one or more of the following types of tasks: simple jump reaction, pursuit tracking, compensatory tracking, divided attention, mental arithmetic coupled with keyboard entry, digit span memory with keyboard entry, and visual flicker discrimination. Unfortunately all of these techniques have at least one of the following disadvantages. They require extensive training of a subject or they test and therefore discriminate on skills not pertinent to driving, such as numerical ability, in addition to discrimination of intoxication. Therefore, they sometimes do not effectively discriminate sober from intoxicated performance. Furthermore, with respect to several tasks mentioned above, as for example jump reaction and mental arithmetic, the performance level in the sober state varies widely among individuals, therefore necessitating the setting of thresholds for each user rather than using a universal threshold. Obviously individual threshold settings present a problem if the equipped vehicle is to be driven by more than one person.

It is the object of this invention, therefore, to provide test equipment that will both more accurately measure those skills pertinent to driving behavior and more effectively discriminate between sober and intoxicated performance.

SUMMARY OF THE INVENTION

The invention is an apparatus for determining a test subject's level of intoxication. Included is a display visible to the test subject and in which is produced by test equipment a pair of randomly moving, spaced apart objects. The test subject operates an actuator to indicate his selections of changing imaginary positions in the display having a predetermined constant spatial relationship to the moving objects. Dynamically determined by a computer system are the actual locations of those positions which are compared with the test subject's selections. Because of the requirement for determining imaginary positions by mental extrapolation, a very rigorous test of the subject's psychomotor capability is obtained. The test does not require, however, special mental abilities that are unrelated to the skill of operating a vehicle.

In a preferred embodiment of the invention the moving objects are optical images that are driven at random velocities in separated but rectilinearly aligned oscillating paths. The test subject is expected to select dynamically the changing mid-points between the randomly moving images and the actual mid-points are determined by the computer system. This selection process is eminently related to the skill required to drive an automobile along a road without collision.

A feature of the invention is the provision of a feedback system for limiting the minimum spacing between the test objects. In response to an occurrence of the predetermined minimum spacing, the velocity of the more rapidly accelerating test object is reversed. The feedback system prevents the undesirable and distracting phenomena that would accompany superposition of the objects.

DESCRIPTION OF THE DRAWINGS

These and other objects and features of the invention will become more apparent upon a perusal of the following description taken in conjunction with the accompanying drawings wherein.

DESCRIPTION OF THE PREFERRED EMBODIMENT

Figure 1:
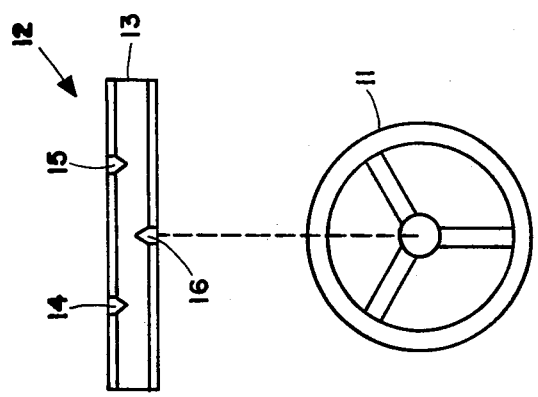
FIG. 1 is a schematic drawing illustrating the relative positions of a display and an operator utilized in the invention.

Referring now to FIG. 1 there is schematically illustrated a rotatable operator wheel 11 that simulates the steering wheel of a vehicle. Positioned so as to be visible to one operating the wheel 11 is a display 12 having a screen 13. Movable along horizontal, rectilinearly aligned paths on the screen 13 are a pair of objects 14 and 15 formed by illuminated images as described in greater detail below. Also movable on the screen 13 along a rectilinear path parallel to the paths of the images 14 and 15 is a third optical image 16. Movement of the image 16 is controlled by the wheel 11 as described hereinafter.

Figure 2:
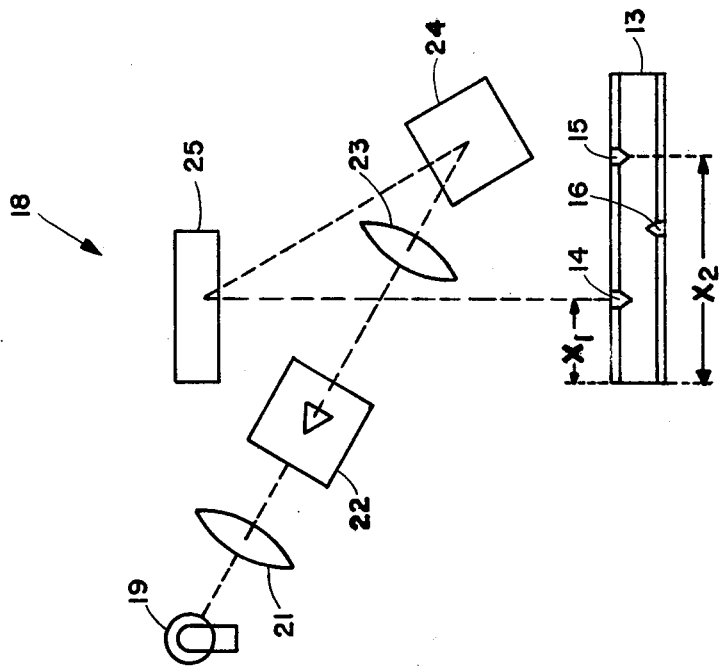
FIG. 2 is a schematic drawing of an optical system utilized to produce images in the display of FIG. 1.

FIG. 2 schematically illustrates an optical system 18 for producing the image 14 shown in FIG. 1. Light from a source 19 is focused by a lens 21 onto a mask 22 producing an indicator image that is transmitted by a lens 23 onto the reflecting surface of a mirror 24. The reflected image from the mirror 24 is again reflected by a mirror galvanometer 25 onto the screen 13 producing the left image object 14. Identical optical systems (not shown) are employed to create the right image object 15 and the subject controlled indicator image 16.

Figure 3:
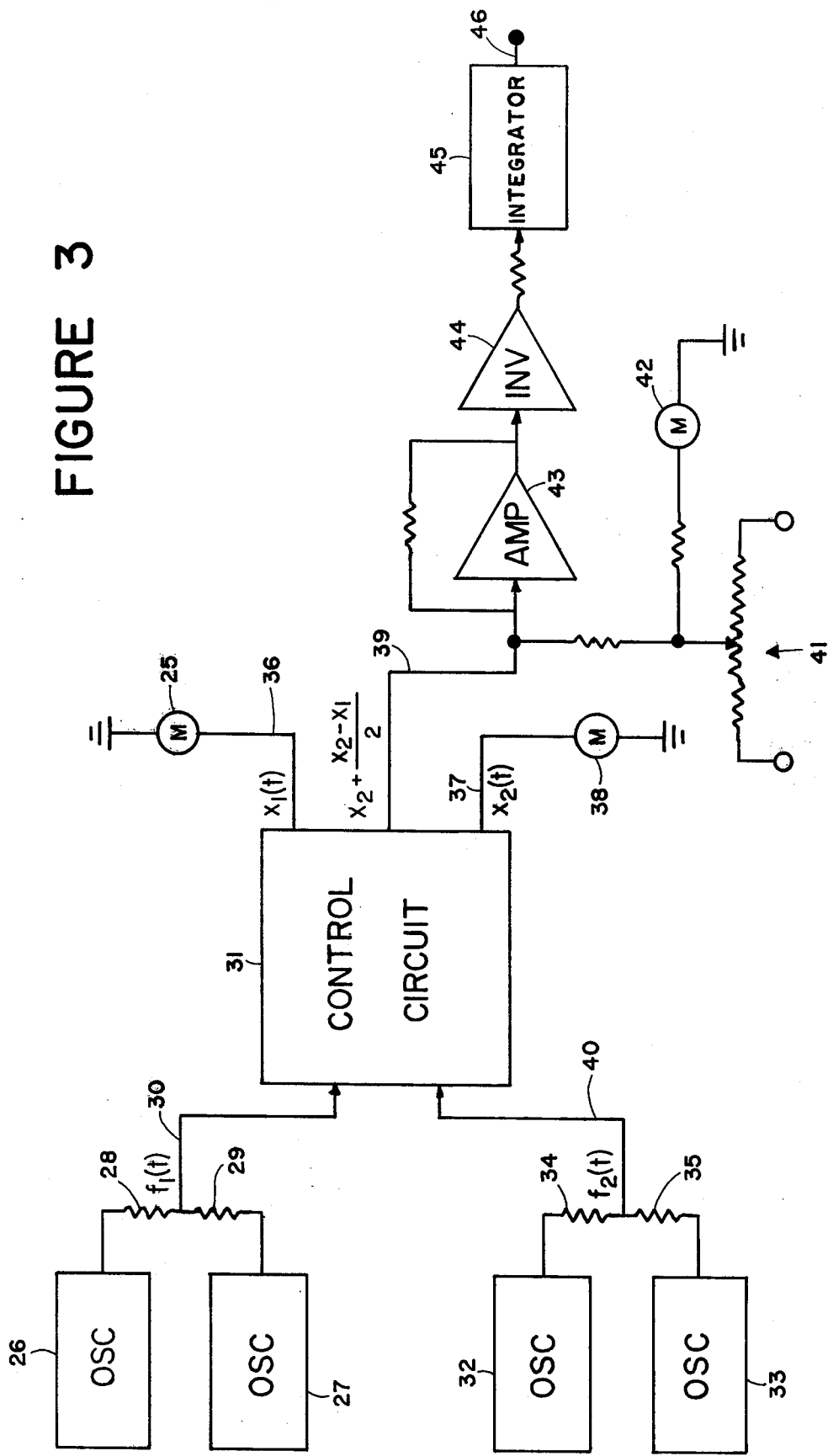
FIG. 3 is a schematic block diagram illustrating an electrical circuit for use with the systems shown in FIGS. 1 and 2.

Movement of the images 14, 15 and 16 on the screen 13 is controlled by an electrical circuit schematically illustrated in FIG. 3. A pair of oscillators 26 and 27 provide inputs to a bridge circuit including a pair of resistors 28 and 29. The oscillators 26 and 27 produce outputs of different frequency and provide at a junction between the resistors 28 and 29 a first forcing function $f_1(t)$ that is applied on a line 30 to a control circuit 31. Another pair of oscillators 32 and 33 provide at a junction between another pair of resistors 34 and 35 a second forcing function $f_2(t)$ that also is applied on a line 40 to the control circuit 31. As described below, the control circuit 31 operates on the forcing functions $f_1(t)$ and $f_2(t)$ to produce a first time variable control voltage $x_1(t)$ on a line 36 and a second time variable control voltage $x_2(t)$ on a line 37. The voltage on the line 36 is applied to the mirror galvanometer 25 and its magnitude establishes the position $x_1$ of the image 14 as shown in FIG. 2. Similarly, the voltage on the line 37 is applied to a mirror galvanometer 38 associated with the image 15 and establishes its position $x_2$.

Also produced by the control circuit 31 on a line 39 is a signal voltage $[x_1 + (x_2 + x_1)/2]$ representing the actual mid-point between the moving images 14 and 15. The voltage on line 39 is differentially combined with the output of a potentiometer 41 that is mechanically coupled to the operator wheel 11 shown in FIG. 1. Also connected to the potentiometer 41 is a third mirror galvanometer 42 of an optical system (not shown) associated with the image 16 and identical to the system 18 shown in FIG. 2. The voltage at the junction 39 is applied to an error detector amplifier 43 that provides an input to an inverting buffer amplifier 44. An integrator 45 receives the output from the inverter 44 producing an error signal on line 46.

During operation of the circuit shown in FIG. 3, the galvanometers 25 and 38 are driven by the voltages $x_1(t)$ and $x_2(t)$ producing random oscillating movement of the images 14 and 15 that is observed by a test subject. Simultaneously, the image 16 is moved on the screen 13 by the galvanometer 42 in response to the output of the potentiometer 41 which is in turn controlled by the operator wheel 11. The test subject manipulates the wheel 11 in an attempt to continuously position the image 16 at the mid-point between the images 14 and 15 and the positions selected by the subject are represented by the voltage output of the potentiometer. When that output equals the output on line 39, the tracking error detector 43 produces a null voltage. Thus, the magnitude of the voltage at the output of the tracking error detector 43 is dependent on how closely the test subject positions the image 16 to the actual mid-point between the moving images 14 and 15. This output voltage is inverted by the inverting buffer 44 before being fed to the integrator 45. Obviously the output of the integrator will increase during the test interval in proportion of the tracking error which can be indicated by a voltmeter (not shown) or used to control an ignition interlock (not shown).

Figure 4:
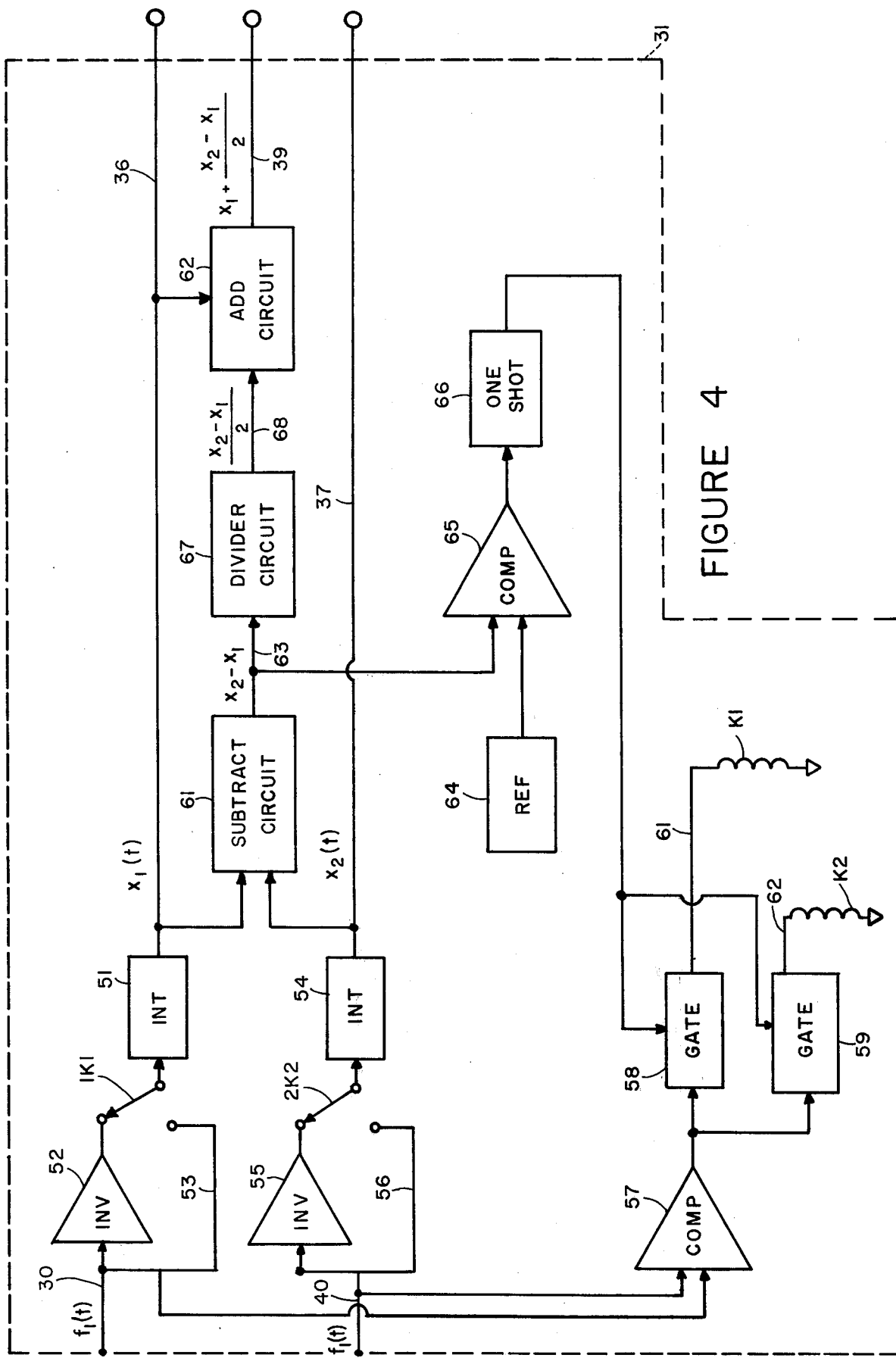
FIG. 4 is a schematic block diagram of an electrical control circuit shown in FIG. 3.

Referring now to FIG. 4, there are shown, in block diagram form, further details of the control circuit 31 shown in FIG. 3. The random signal on the line 30 is fed into an integrator 51 by either an inverter 52 or a line 53 depending upon the position of a switch contact 1K1. Similarly the random signal on the line 40 is fed into an integrator 54 by either an inverter 55 or a line 56 depending upon the position of a switch contact 2K2. Comparing the signal levels on lines 30 and 40 is a comparator 57 that provides signal inputs to a pair of gates 58 and 59. The gate 58 is enabled by the comparator 57 in response to the presence of a larger signal on line 30 and the gate 59 is enabled by the comparator 57 in response to the presence of a larger signal on line 40. Receiving the outputs of the gates 58 and 59 on lines 61 and 62, respectively, are a relay winding K1 associated with the switch contact 1K1 and a relay winding K2 associated with the switch contact 2K2.

The output of the integrator 51 is a time variable voltage $x_1(t)$ that appears on the line 36 and is applied to the first galvanometer mirror 25 shown in FIG. 2. That voltage is also applied to a subtract circuit 61 and to an add circuit 62. Similarly the output of the integrator 54 is a time variable voltage $x_2(t)$ that appears on the line 37 and is applied to the second galvanometer 38 shown in FIG. 3. That signal is also applied to the subtract circuit 61 that produces on a line 63 a difference voltage representing the total spacing $x_2 - x_1$ between the test objects 14 and 15 (FIG. 2). The difference voltage on line 63 is compared to a reference voltage from a reference source 64 by a comparator 65. In response to a difference signal magnitude on the line 63 less than the signal magnitude from the reference 64, the comparator 65 fires a one shot 66 that in turn applies a triggering voltage to both of the gates 58 and 59. Also receiving the difference voltage on the line 63 is a divider circuit 67 that produces on a line 68 a signal voltage $(x_2 - x_1)/2$ representing one-half the spacing between the test objects 14 and 15. That signal is received by the add circuit 62 that produces on the line 39 a signal $x_1 + (x_2 - x_1)/2$ representing the actual midpoint between the test objects 14 and 15.

During use of the test apparatus, the randomly variable voltage outputs of the integrators 51 and 54 drive the test objects 14 and 15 along oscillating rectilinearly aligned paths on the screen 13 as described above. Simultaneously, the outputs of the add circuit 62 representing the actual changing mid-points between the test objects 14 and 15 are compared to the positions of the operator image 16 selected by the test subject. Should the spacing between the test objects 14 and 15 decrease to a predetermined minimum established by the setting of the reference source 64, the negative threshold level on the signal line 63 causes the comparator 65 to fire the one shot 66. The resultant output of the one shot 66 triggers whichever of the gates 58 or 59 that has been enabled by the comparator 57. As described above, the comparator 57 enables the gate 58 in response to a larger signal on the line 30 and enables the gate 59 in response to a larger signal on the line 40. These signals represent the levels at which the test objects 14 and 15 are accelerating. Assuming that gate 58 is triggered, energization of the relay winding K1 actuates the switch contact 1K1 to a position opposite to that then occupied. In response to this switching the polarity applied to the integrator 51 is reversed to thereby reverse the direction in which the first test object 14 is moving. Similarly, triggering of the gate 59 energizes the winding K2 to actuate the switch contact 2K2 to a position opposite to that then occupied. The effect of this switching is to reverse the polarity applied to the integrator 51 and thereby reverse the direction of movement of the second test object 15. Therefore, the control circuit 31 responds to the occurrence of the given minimum spacing between the test objects 14 and 15 by automatically reversing the direction of movement of the most rapidly accelerating object, thereby preventing a further reduction in spacing. For this reason any undesirable and distracting superposition of the test objects is prevented.

Obviously, many modifications and variations of the present invention are possible in light of the above teachings. For example, although described in conjunction with use as an intoxication level tester, the apparatus could be used to test psychomotor response in other applications. Also, a variation of the invention comprises the use of mechanical rather than optical systems and modifications of the task are numerous. For instance, tracking could be required at various ratios of the distance between the moving objects. Also, the moving objects could be oriented in a variety of directions; there could be more than two moving objects; instead of two objects, there could be a randomly expanding and contracting perimeter or even volume designed in a variety of shapes. The required task could be to track the center (or elsewhere) of the shape or volume. Moreover, within trails, the difficulty of the task could be increased or altered to obtain measures of maximal performance. It is to be understood, therefore, that the invention can be practiced otherwise than as specifically described.

What is claimed is:

1. An intoxication testing apparatus comprising:
   display means for producing a display visible to a test subject;
   first test means for producing a first moving object in said display;
   second test means for producing a second moving object in said display;
   computer means for dynamically determining the changing locations of the midpoint of given positions between said moving objects and having a constant spatial relationship thereto;
   actuator means operable by the subject to dynamically select particular positions between said moving objects; and
   comparator means for dynamically comparing the locations of said given and particular positions.

2. Apparatus according to claim 1 wherein said comparator comprises integrator means for integrating the differences in location between said given and particular positions.

3. Apparatus according to claim 1 including feedback limit means for limiting the minimum separation of said moving objects.

4. Apparatus according to claim 3 wherein said feedback limit means comprises reversal means for reversing the direction of movement of one of said moving objects in response to the occurrence of a given minimum separation therebetween.

5. Apparatus according to claim 4 wherein said first and second test means produce oscillating movement of said objects along rectilinearly aligned paths.

6. Apparatus according to claim 5 wherein said objects are images and said first and second test means comprise image generation means.

7. Apparatus according to claim 6 wherein said first and second test means comprise random generator means for producing random movement of said images.

* * * * *